United States Patent [19]

Zoltewicz et al.

[11] Patent Number: 5,602,257

[45] Date of Patent: Feb. 11, 1997

[54] SYNTHESIS OF NICOTINIC ANALOGS

[75] Inventors: John A. Zoltewicz; Michael P. Cruskie, both of Gainesville, Fla.

[73] Assignee: University of Florida Research Foundation, Gainesville, Fla.

[21] Appl. No.: 304,100

[22] Filed: Sep. 9, 1994

Related U.S. Application Data

[63] Continuation-in-part of PCT/US92/01451 Feb. 27, 1992 which is a continuation-in-part of Ser. No. 662,867, Mar. 1, 1991, abandoned.

[51] Int. Cl.⁶ .................................................. C07D 401/04
[52] U.S. Cl. .......................... 546/193; 546/194; 546/257; 514/318; 514/334
[58] Field of Search ........................... 546/193, 194, 546/257; 514/318, 334

[56] References Cited

U.S. PATENT DOCUMENTS 5,109,017  4/1992  Schmiesing ............................. 514/438

OTHER PUBLICATIONS

McOmie "Protective groups in organic chemistry" Plenum Press, p. 61 (1973).
Pathak et al "Synthesis of [4-²H₂]- ,(4R)[4-²H₁] 4-Methyl nitrosamino)-1-(3'pyridyl)-1-Butauone" Tetrahedron 46 1733-1744 (1990).
Zoltewicz et al "Hydrolysis of cholinergic anabaseine and N-methyl anabaseine" Bio org. Chem. 18 395-412 (1990).
Zoltewicz et al "Quantitative Determination of Riz-Chain Hydrolysis Equilibrium" J. Org. Chem. 54 4462-68 (1989).
Castonguay et al "Synthesis of C¹⁴ Labelled 4-methylnitrosamino 1-(3-pyridyl)-1-Butauone" J. Lab. Comp.d. 22 23-28 (1985).
Wiley et al "Synthesis of 4-(Methynitrosamino)-1-(3-pyridyl)-1-Butauone" J. Labelled. Compd. 25 707-716 (1988).
Hamlet et al "1-(dialkylaminomethyl)-azetidin-2-ones" Can. J. Chem. 61 411-415 (1983).
Buehler et al "Organic Synthesis" Wiley Interscience, pp. 461-462 (1970).
Meyer, et al., Effects of Nucleus Basalis Lesions on the Muscarinic and Nicotinic Modulation of [³H]Acetylcholine Release in the Rat Cerebral Cortex, Journal of Neurochemistry, pp. 1758-1762, vol. 49, No. 6, 1987.

Kem, Structure and Action of Nemertine Toxins, American Zoology, 25:99-111, 1985.
Zoltewicz, et al., Quantitative Determination of the Ring–Chain Hydrolysis Equilibrium Constant for Anabaseine and Related Tobacco Alkaloids, Journal of Organic Chemistry, vol. 54, No. 18, pp. 4462–4468, 1989.
Kem, et al., Hoplonemertine Worms—a New Source of Pyridine Neurotoxins, Experientia, pp. 684–686, 1976.
Kem, Pyridine Alkaloid Distribution in the Hoplonemetines,. Hydrobiologia 156:145–151, 1988.
Kem, Worm Toxins, Handbook of Natural Toxins. vol. 3, pp. 353–378, 1988.
Kem, et al., Isolation and Structure of a Noplonemertine Toxin, Toxicon, vol. 9, pp. 15–22, 1971.
Kem, Biochemistry of Nemertine Toxins, Marine Pharmacognosy, Chapter II, pp. 37–84, 1973.
Kem, A Study of the Occurrence of Anabasine In Paranemertes and Other Nemertines, Toxicon, vol. 9, pp. 23–32, 1971.
Waters, Cognitive Enhancing Agents: Current Status in the Treatment of Alzheimer's Disease, Le Journal Canadien Des Sciences Neurologiques, 15:pp. 249–256, 1988.
Castonquay & Hecht, Synthesis of Carbon–14 Labeled 4-(Methylnitrosamino)-1-(3-Pyridyl)-1-Butanone¹, Journal of Labelled Compounds and Radiopharmaceuticals, No. 1, 22:23–28, Jul. 16, 1984.

*Primary Examiner*—Ceila Chang
*Attorney, Agent, or Firm*—Arnold, White & Durkee

[57] ABSTRACT

A novel synthesis of anabaseine using an animal nicotinoyl piperidone salt having the formula:

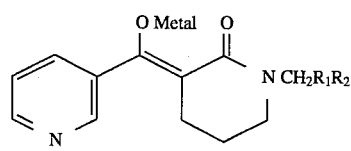

wherein $R_1$ and $R_2$ are lower alkyl, or $R_1$ and $R_2$ forms a morpholine or piperidine ring and the metal is a group I alkaline metal.

17 Claims, 4 Drawing Sheets

SYNTHESIS OF NICOTINIC ANALOGS

RELATED PATENT APPLICATIONS

This application is a Continuation-in-Part of PCT Patent Application Ser. No. PCT/US92/01451, filed Feb. 27, 1992, which is a Continuation-in-Part of U.S. Ser. No. 07/662,867, filed Mar. 1, 1991, now abandoned.

BACKGROUND OF THE INVENTION

1. Field of the Invention

This invention relates to anabaseine, DMAB-anabaseine, and anabasine and their use to treat degenerative diseases of the nervous system.

2. Description of Related Art

It has long been customary in classifying diseases of the nervous system to group them as degenerative, thereby indicating they are characterized by a gradually evolving, relentlessly progressive, neuronal death. Science has shown that a considerable portion of disorders that are classed as degenerative are associated with genetic predisposition which results in a pattern of dominant or recessive inheritance. However, others, although they do not differ in a fundamental way from the hereditary disorders, may occur only sporadically as isolated instances within a given family.

As a consequence, since by definition, classification of degenerative diseases cannot be based upon exact knowledge of their cause or pathogenesis, subdivision of these diseases into individual syndromes rests upon descriptive criteria based largely upon pathologic anatomy and consideration of clinical aspects. As a result, this group of diseases presents itself in the form of several clinical syndromes. However, apart from the general differences that allows the distinction of one syndrome from another, there are certain general attributes which typify this entire class of disorders.

The degenerative diseases of the nervous system can typically be divided into disorders characterized by progressive dementia in the absence of other prominent neurologic signs (e.g., Alzheimer's disease, senile dementia, and Pick's disease); syndromes which combine progressive dementia with other prominent neurologic abnormalities (e.g., Huntington's disease, Hallervorden-Spatz, and progressive familial myoclonic epilepsy); syndromes of gradually developing abnormalities of posture and movement (e.g., Parkinson's disease, striatonigral degeneration, torsion dystonia, and Gilles de la Tourette syndrome); syndromes of progressive ataxia (e.g., cerebellar cortical degeneration, olivopontocerebellar atrophy, and Friedreich's ataxia); and syndromes of muscular weakness and wasting without motor neuron disease (e.g., amyotrophic lateral sclerosis, spinal muscular atrophy, and hereditary spastic paraplegia), to name but a few.

Among those diseases listed above, perhaps those most familiar are Alzheimer's and Parkinson's diseases. These diseases are progressive neurological disorders characteristically associated with aging. Alzheimer's disease is characterized by a profound loss of memory and other cognitive functions, while Parkinson's disease is an extrapyramidal movement disorder. Both are invariably fatal. Although there is no effective treatment for Alzheimer's disease, clinical trials are underway with several drugs that increase brain cholinergic transmission. In Parkinson's disease, several treatments are temporarily useful, notably L-DOPA related therapies that replace dopamine in the nigrostriatal pathway. However, in Parkinson's disease the therapeutic efficacy of even the best drugs is temporary at best.

Although the loss of neurons in the late stages of Alzheimer's disease is profound, only a few neuronal pathways appear to be affected in its earliest stages. These include cholinergic projections from the nucleus basalis to the cerebral cortex and from the septum to the hippocampus, noradrenergic projections from the locus cerululus to the cerebral cortex, and several peptidergic neurons that are probably intrinsic to the cerebral cortex. The loss of the aforementioned cholinergic pathways in particular is believed to underlie the early memory loss, since these pathways are known to be important for memory and cognition. This association accounts for the major emphasis in novel cholinergic treatments for Alzheimer's disease, at least in its early stages.

A recent study on Alzheimer's disease demonstrated that loss of cholinergic projections from the nucleus basalis to the cerebral cortex was sufficient, after extended intervals, to cause trans-synaptic neuron loss in the rat. Thus, it is conceivable that the early loss of analogous cholinergic neurons in Alzheimer's disease could cause a profound cascade phenomenon resulting in the loss of many neurons over a period of years. If so, then replacement therapy might not only improve survival of these neurons, but perhaps more important, keep other brain cells from dying.

Given the possibility of such therapy, it is of primary importance to determine the type of cholinergic agent most likely to improve memory and/or keep brain neurons from dying after the loss of cholinergic neurons. To address this issue, it is necessary to consider the two general types of cholinergic transmission in the brain. One is termed muscarinic, the other nicotinic. These terms are based on the type of receptor to which acetylcholine binds to in order to elicit its neurotransmitter effect. In brain regions associated with memory, the muscarinic receptors predominate quantitatively over the nicotinic receptors, although both types coexist. For this reason, most investigators traditionally focused on the development of muscarinic agonists to improve memory-related behaviors. These agents have been found to have moderate effects in rats with lesions of the nucleus basalis, but have little effect in patients with pronounced Alzheimer's disease.

There is reason to believe, however, that nicotinic transmission may also be important for treating Alzheimer's disease. This is supported by the fact that cerebral cortical nicotinic receptors decrease significantly during the disease, while post-synaptic muscarinic receptor levels are often unchanged. These observations are consistent with the hypothesis that neurons expressing nicotinic receptors are lost in the disease. When these observations are combined with those of the present inventors, that lesions of ascending cholinergic neurons from the nucleus basalis cause a trans-synaptic neuron loss in the cortex, it is hypothesized that the neurons in the cortex that die trans-synaptically (and in Alzheimer's disease) do so because they do not receive enough nicotinic stimulation. For this reason, the inventors believe nicotinic agents may be useful as replacement therapy for keeping brain neurons alive in Alzheimer's disease that would otherwise die from lack of nicotinic transmission. An analogous situation exists in several other systems such as: (a) muscle cells, which atrophy in the absence of nicotinic activation; (b) sympathetic ganglia, which require either nerve growth factor or nicotinic transmission (in the presence of calcium ions) in order to survive in culture; and (c) nigrostriatal dopamine neurons, which appear to be partially spared by nicotine following lesions of the substantia nigra. Also, it is important to note that there exist several types of nicotinic receptors in the brain, which allows considerable potential selectivity in targeting drugs for certain nicotinic sites.

The observation that nicotine treatment can preserve nigrostriatal dopamine neurons in an animal model for Parkinson's disease is consistent with epidemiological evidence that there is a lower incidence of this disease in cigarette smokers (even after adjusting for the smoking-induced increase in mortality). The mechanism whereby nicotine can preserve these neurons is not known, but it does appear to involve effects of nicotinic transmission on dopamine neurons themselves, since these neurons possess this type of cholinergic receptor. While the remainder of this patent application focuses on the potential treatment of Alzheimer's disease with nicotinic receptor agents, it should be noted that these drugs may be just as effective, or more so, on dopaminergic neurons that are lost in Parkinson's disease.

Nicotine has been used in several clinical trials for the treatment of Alzheimer's disease, primarily over rather short intervals for its potential memory enhancing effect (not for its ability to block long term trans-synaptic cell loss). In one recent study, nicotine had a marginally positive effect on memory and an even greater one of improving the mood of the patients. These positive results have not been followed up with longer term ones, however. Unfortunately, while nicotine has a history of improving memory related behaviors in humans and animals, its potent toxicity, low effective dose range, and peripheral side effects, have basically rendered it unacceptable for treating Alzheimer's disease.

Thus, considerable need exists for agents which stimulate cholinergic transmission, but, unlike nicotine, are relatively non-toxic. The present invention provides a method of using agents which have this capability.

SUMMARY OF THE INVENTION

The present invention arose out of the discovery that anabaseine, DMAB-anabaseine, and anabasine could be used to improve overall brain neurocortical cholinergic activity. The interaction of these agents with nicotinic receptors has decreased levels of toxicity as compared to nicotine.

In the absence of long term studies for the clinical effectiveness of nicotine or its analogs for Alzheimer's or Parkinson's disease, the present invention has developed the nucleus basalis lesioned rat as a model for trans-synaptic neuronal degeneration caused by the loss of ascending neurons. Bilateral lesions of cholinergic neurons in the nucleus basalis were induced with ibotenic acid to cause long-term, essentially irreversible deficits in neocortical choline acetyltransferase activity, an enzyme selective for cholinergic neurons. However, passive avoidance behavior, a learning and memory paradigm particularly sensitive to nucleus basalis-lesions, reportedly recovers to normal levels sometime between 2–8 months post-lesioning.

A novel synthesis of nicotinic analogs is provided that avoids the use of expensive materials and costly low temperature process conditions.

Various other aspects and attendant advantages of the present invention will be more fully appreciated from an understanding of the following detailed description in combination with the accompanying examples.

DETAILED DESCRIPTION OF THE INVENTION

Figure 1:
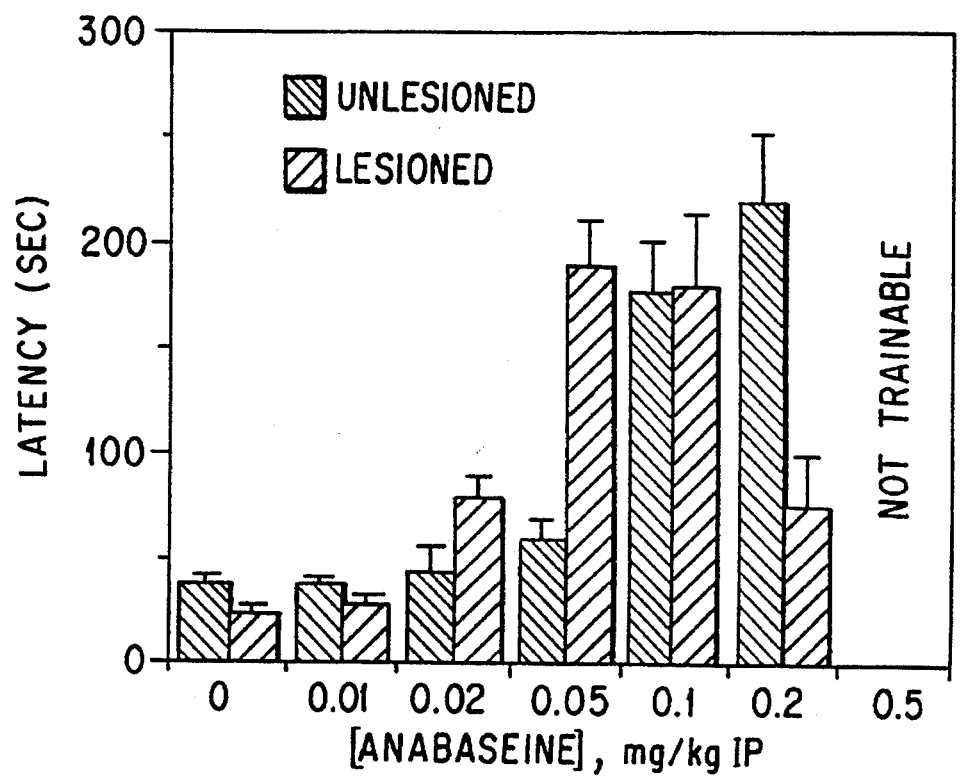
FIG. 1 Effects of NBM lesions on anabaseine-induced improvement in passive avoidance behavior.

Anabaseine, 2-(3-pyridyl)-3,4,5,6-tetrahydropyridine, occurs in certain marine worms, which use the substance to paralyze prey and deter predators (Kem, et aL, *Toxicon,* 9:23, 1971). Anabaseine is a potent activator of vertebrate neuromuscular nicotinic acetylcholine receptors (Kem, *Amer. Zoologist,* 25:99, 1985). Both nicotine and anabaseine possess a non-aromatic ring attached to the 3-position of a pyridyl ring. Anabaseine's non-aromatic tetrahydropyridine ring imine double bond is conjugated with $\pi$-electrons of the 3-pyridyl ring. The imine nitrogen is a much weaker base than the pyrrolidinyl nitrogen of nicotine (Yamamoto, et al., *Agr. Biol. Chem.,* 26:709, 1962). Considerable evidence (Barlow and Hamilton, *Brit. J. Pharmacol.,* 18:543, 1962) exists that the non-aromatic ring nitrogen of nicotine must be protonated (cationic) in order to avidly bind to the skeletal muscle nicotinic receptor and activate the opening of its channel. At physiological pH, anabaseine also exists in a hydrolyzed ammonium-ketone form as well as the cyclic imine (unionized) and cyclic iminium (monocationic) forms. The inventors have determined that anabaseine acts as a central nicotinic receptor agonist primarily through its cyclic iminium form.

The synthesis of anabaseine was first reported in 1936 (Spath, et al., *Chem. Ber.,* 69:1082, 1936). Unfortunately, this technique utilized an elaborate isolation scheme involving a distillation and preparation of a picrate. Medicinally, the picrate is of no useful value, in fact, since picrate is toxic and potentially explosive, its presence precludes the direct use of anabaseine in physiological systems when produced by this technique.

The first analog of anabaseine to be synthesized was 2-(3-pyridyl)-3-(4-dimethylamino-benzylidene)-delta 1,2-piperidine, also termed DMAB-anabaseine (Kem, et al., *Toxicon,* 9:23, 1971). This compound, resulting from the electrophilic attack of Ehrlich's reagent upon anabaseine, is a stable orange-colored compound.

The present invention provides an improved method for synthesizing anabaseine which overcomes the problems associated with prior disclosed techniques for its synthesis.

The first part of the improved synthesis of anabaseine, the joining of an activated derivative of nicotinic acid and a modified 2-piperidone, is performed using a mixed Claisen condensation. The second part of the synthesis involves the hydrolysis and decarboxylation of the condensed product. The overall reaction sequence is shown below.

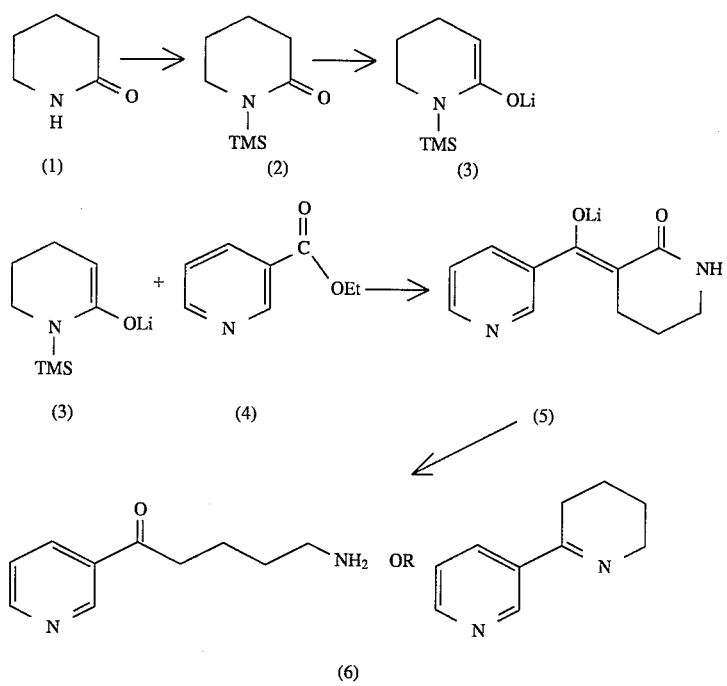

In the scheme presented herein, certain protecting and activating groups are specifically illustrated. However, one skilled in the art will recognize that other protecting and activating groups could have been used. For example, a variety of amino protecting group can be used to protect the nitrogen of 2-piperidone (1). Representative amino protecting groups are $C_1$–$C_4$ alkanoyl, benzyl, and trialkylsilyl derivatives such as trimethylsilyl and butyldimethylsilyl. The preferred amino protecting group is trimethylsilyl (TMS). The TMS-protected 2-piperidone (2) is prepared by deprotonation and subsequent reaction with trimethylchlorosilane. Typical silylation conditions are the use of lithium diisopropylamide (LDA) in an inert solvent such as tetrahedrofuran (THF) at –70° C. For each one mole of 2-piperidone, at least one mole of LDA, preferably 1½ moles, should be used to ensure complete silylation. While maintaining the temperature at –70° C., at least one molar equivalent of TMS is combined with the LDA-added reaction mixture. Normally, silylation is complete within a few hours by raising the reaction temperature to ambient temperature.

The protected 2-piperidone (2) is next enolyzed to an enolate by base. Conveniently, this enolization can be conducted by simply adding additional LDA to the reaction mixture containing compound (2). Although this is a preferred process, other suitable bases which can be employed include metal amides such as $NaNH_2$ or $KNH_2$, metal hydrides such as NaH or KH, and metals such as Na or K. In practice, the reaction mixture is cooled to –70° C., at which point at least one molar equivalent of LDA is added. Enolization is usually complete within an hour, and the resultant amide enolate (3) can be directly used in the next condensation reaction.

The key Claisen condensation between a 2-piperidone enolate and a nicotinic acid derivative can be carried out, e.g., by combining the lithium amide enolate (3) in an inert solvent such as THF with about one molar equivalent of ethyl nicotinate. Reaction temperature can be varied, but it is preferred to start the condensation at –70° C. and to allow the temperature to warm up to ambient temperature. Reaction requires a few hours to 24 hours until its completion.

Although an ethyl ester form of nicotinic acid (4) has been illustrated hereinabove, activation of the carboxylic group to expedite condensation can be achieved by other activating groups known in the art. Especially useful in the herein described condensation are anhydrides, particularly cyclic anhydrides, acid halides, and activated esters such as those derived from N-hydroxysuccimide and N-hydroxypthalimide. Alkyl esters of up to $C_5$ other than ethyl ester can also be used.

The condensed product (5) is isolated after removal of TMS group by hydrolysis. The product (5) is normally subjected to hydrolysis and decarboxylation without further purification.

Conversion of compound (5) to the final anabaseine (6) is accomplished by first hydrolyzing compound (5) with a strong acid such as concentrated hydrochloric acid; and by second decarboxylating the intermediate/β-keto acid (not shown in the above scheme). Both hydrolysis and decarboxylation steps are conveniently conducted in one-pot in the presence of concentrated hydrochloric acid at an elevated temperature, e.g., under reflux. Anabaseine (6) is thus obtained as its dihydrochloride.

In an additional preferred embodiment of this invention the synthesis of anabaseine is accomplished without the need for costly starting materials and low reaction temperatures. In this embodiment of the invention the protected 2-piperidone is an aminal derivative, and the mixed Claisen condensation is performed using sodium hydride in toluene according to the following reaction scheme:

New Synthesis of Anabaseine

2-Piperidone protected as the aminal

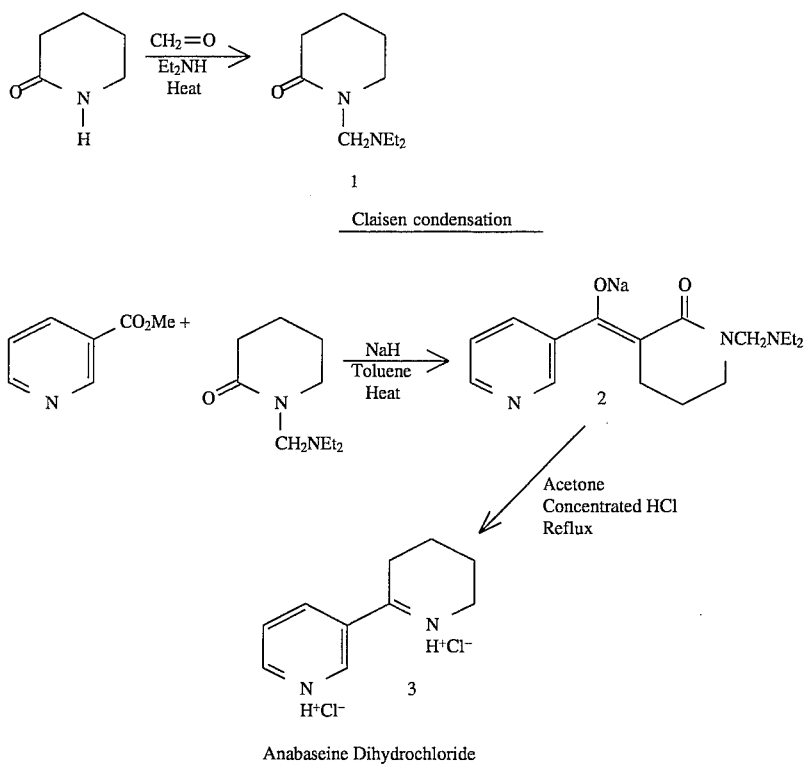

Anabaseine Dihydrochloride

A mixture of 2-piperidone, formaldehyde, and a secondary amine are heated together to reflux and then concentrated. The formaldehyde is preferably selected from the group consisting of an aqueous solution of formaldehyde, anhydrous formaldehyde as its acetal, and paraformaldehyde. The secondary amine is preferably selected from the group consisting of diethylamine, morpholine, and piperidine. The reaction initially is exothermic upon addition of the secondary amine. The aqueous phase is extracted with an organic cosolvent, such as diethyl ether, present in a molar excess relative to the sodium salt, dried, and concentrated. The product aminal of 2-piperidone (1) is purified, such as by vacuum distillation. Alternatively, the product can be distilled over after refluxing so as to eliminate the extraction step.

To a solution of the aminal is added ethyl nicotinate, a solvent selected from the group consisting of toluene, 1,4-dioxane, tetrahydrofuran, ethylene glycol, and dimethyl ether, and an excess of sodium hydride to form a suspension. The sodium hydride can be added as a dispersion in oil or as a dry powder. The suspension is heated at reflux while stirring, and a gas is evolved. After about four hours of reflux, another equivalent of sodium hydride is added, and reflux is continued, usually for another equal period of time. The product is filtered to remove excess NaH, which can be destroyed by cautious addition of an alcohol such as ethanol or isoproply alcohol. The filtrate is cooled, usually to 0° C., to precipitate out the sodium salt of the aminal (2). The precipitate is collected by filtration and dried to yield a mixture of enol and keto tautomers of the sodium salt.

The sodium salt (2) is heated at reflux for about 12 hours with concentrated strong acid, preferably HCl. To obtain a preferred yield, the concentrated strong acid is mixed with a carbonyl compound such as a low molecular weight ketone, such as acetone or methyl ethyl ketone, preferably acetone, in molar excess relative to the sodium salt (2) in order to trap the liberated formaldehyde. The preferably ratio of the carbonyl compound to the sodium salt is about 5:1. The filtrate is diluted with a $C_2$ to $C_4$ alcohol, preferably isopropyl alcohol, and allowed to sit at 0° C. while the anabaseine dihydrochloride (3) slowly crystallizes out.

Anabasine is commercially available from Aldrich Chemical Co. Alternative sources of anabasine are reduction of anabaseine.

Reduction of anabaseine to anabasine can be achieved by several ways: (1) Hydrogeneration with hydrogen over Pd/C, as described in E. Spath, et aL., *Chem. Ber.*, 69:1082 (1936); (2) Borohydride reduction with either $NaBH_3CN$ or with $NaBH_4$, as described in E. Leate, *J. Org. Chem.*, 44:165 (1979); and (3) Reduction with hot formic acid.

Anabasine having the following formula contains an asymmetric center at the 2-carbon of the piperidine ring.

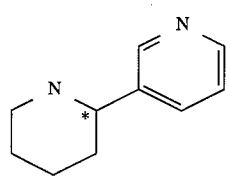

Thus, anabasine can exist as an optically active form. The present invention embraces such optically pure anabasine, the pure enantiomers thereof, and the racemate thereof.

Anabaseine and anabasine in their free base form will form acid addition salts, and these acid addition salts are non-toxic and pharmaceutically acceptable for therapeutic use. The acid addition salts are prepared by standard methods, for example by combining a solution of anabaseine or anabasine (base) in a suitable solvent (e.g., water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent or, in the case of aqueous solutions, by dyophilization. Of particular value are the sulfate, hydrochloride, hydrobromide, nitrate, phosphate, citrate, tartrate, pamoate, perchlorate, sulfosalicylate, benzene sulfonate, 4-toluene sulfonate and 2-naphthalene sulfonate salts. These acid addition salts are considered to be within the scope and purview of this invention.

As a result of using the above method for the synthesis of anabaseine: (1) the chemistry is cleaner and simpler; (2) higher yields of anabaseine are obtained; and (3) picric acid is not present, such that a more directly pharmacologically useful form of anabaseine is produced.

The term "therapeutically effective" means that the amount of nicotinic receptor agent used is of sufficient quantity to increase brain cholinergic transmission. The dosage ranges for the administration of the agent of the invention are those large enough to produce the desired effect in which the nicotinic receptors show some degree of stimulation. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any contraindications. Dosage can vary from about 10 µg/kg/dose to about 100 µg/kg/dose, preferably from about 30 µg/kg/dose to about 70 µg/kg/dose, most preferably from about 50 µg/kg/dose to about 60 µg/kg/dose in one or more dose administrations daily, for one or several days. Alternatively, the dosage can be administered indefinitely in order to prevent a recurrence of cognitive function loss, for example, by administration of the agent in a slow-release form.

The nicotinic receptor agent of the invention can be administered parenterally or by gradual perfusion over time. The nicotinic receptor agent of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In order to form a pharmaceutically acceptable composition suitable for effective administration, such compositions will contain an effective amount of the nicotinic receptor agent, together with a suitable amount of a carrier vehicle.

Additional pharmaceutical methods may be employed to control the duration of action. Controlled release preparations may be achieved by the use of polymers to complex or adsorb the nicotinic receptor agent. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the nicotinic receptor agent into particles of a polymeric material such as polyesters, polyamino acids, hydrogels, poly (lactic acid) or ethylene vinylacetate copolymers. Alternatively, instead of incorporating the nicotinic receptor agent into these polymeric particles, it is possible to entrap the nicotinic receptor agent in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences* (17th Ed., A. Oslo, ed., Mack, Easton, Pa., 1985).

The invention also relates to a method for preparing a medicament or pharmaceutical composition comprising the nicotinic receptor agent of the invention, the medicament being used for therapy to stimulate brain cholinergic transmission.

The above disclosure generally describes the present invention. A more complete understanding can be obtained by reference to the following specific examples which are provided herein for purposes of illustration only, and are not intended to limit the scope of the invention.

EXAMPLE 1

SYNTHESIS OF ANABASEINE

A dihydrochloride crystalline form of anabaseine was prepared via the initial synthesis of 3-nicotinoyl-2-piperidine enolate which was then hydrolyzed and decarboxylated to yield anabaseine.

1) Preparation of 3-Nicotinoyl-2-piperidine Enolate

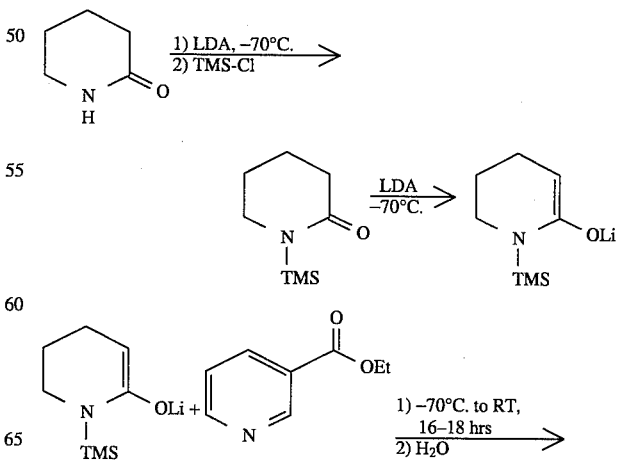

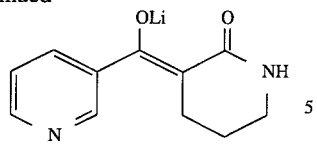

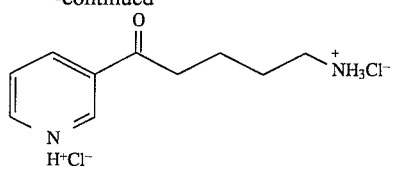

a) Reaction

A 250 mL flask equipped with a nitrogen inlet was flame dried and charged with nitrogen. Dry THF (40 mL) was added to this flask and cooled to −70° C. in a dry ice/acetone bath before 38 mL (57 mmol, 1.5 eq) of 1.5M LDA in cyclohexanes (from Aldrich) was added. A solution of 5.68 g (57.3 mmol, 1.5 eq) of 2-piperidine (previously dried) in 15–20 mL of THF (distilled from sodium and benzophenone to dry) was added through a cannula over a period of 20 min to the stirring LDA solution at −70° C. to form the deprotonated amide.

While stirring the reaction mixture at −70° C., 7.2 mL (56.7 mmol, 1.5 eq) of trimethylsilyl chloride was added through an oven-dried syringe all at once. The resulting solution was stirred at −70° C. for 15 rain and at room temperature for 2 hrs to form the TMS protected piperidine. The solution turned milky colored and a solid precipitate (thought to be LiCl) formed after a few minutes at −70° C. The precipitate dissolved and the solution was clear yellow at room temperature. The reaction mixture was cooled back down to −70° C., before another 38 mL (57 mmol, 1.5 eq) of 1.5 M LDA was added with stirring to form the amide enolate. After stirring the reaction mixture at −70° C. for 20 rain, 5.2 mL (38 mmol, 1 eq) of ethyl nicotinate was added. The reaction mixture was stirred vigorously at −70° C. for 20 min and at room temperature for 17 hrs. After stirring at room temperature for 30 rain the reaction mixture was cloudy and after 90 min the reaction mixture contained a precipitate. The yield can be increased if 2 equivalents of the protected 2-piperidone enolate are used instead of 1.5 equivalents.

After stirring for 17 hrs at room temperature, the reaction mixture was thick with cream colored precipitate (product). Water (50 mL) was added and the reaction mixture was stirred for 15 min to hydrolyze the TMS protecting group. The thick pasty precipitate was filtered out of the reaction mixture. The precipitate appeared to pick up water on standing but then formed a stable pale yellow solid. The solid was dried in a drying pistol to yield 8.060 g of pale yellow powdery solid product (mp>250° C.). This solid was used without further purification.

The remaining phases (water and organic) from the reaction mixture can be checked for product using ferric nitrate $(Fe(NO_3)_3)$. An aqueous solution of ferric nitrate turns dark blue or purple in the presence of a compound. Add a couple drops of ferric nitrate solution to a neutralized sample of the aqueous or organic phases from the reaction mixture to check for additional product.

2) Hydrolysis/Decarboxylation of 3-Nicotinoyl-2-piperidone Enolate to Anabaseine

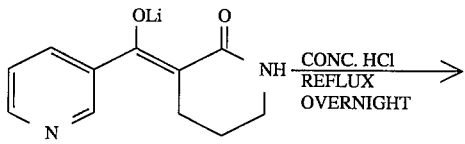

a) Reaction

The lithium enolate of 3-nicotinoyl-2-piperidone (4.94 g) of step 1 was added slowly to a round bottom flask containing 30 mL of concentrated HCl which was chilled in an ice bath and stirred. The enolate was not readily soluble. The reaction mixture was heated at reflux under nitrogen overnight to effect the hydrolysis and decarboxylation. The product, anabaseine dihydrochloride, was very water soluble. The reaction should not be diluted with too much aqueous acid or the product will not crystallize during the work up.

Next, the reaction mixture was cooled to room temperature and diluted slowly with isopropyl alcohol to a volume of about 350 mL. The isopropyl alcohol solution was cooled in the refrigerator and the product slowly crystallized. The solution was allowed to warm to room temperature before filtering the 3.88 g of white needle-like crystalline solid (mp 173°–178° C., decomp). The filtrate was cooled in the refrigerator to yield 0.209 g of a second crop of product.

The first crop of solid was recrystallized by adding it to about 200 mL of hot isopropyl alcohol and adding 6M HCl slowly to the boiling mixture until all of the solid dissolved (about 5 mL of HCl was added). After cooling the solution in the refrigerator, 3.26 g of anabaseine dihydrochloride was collected (mp 175°–180° C., decomp). Anabaseine dihydrochloride was prepared in 56% overall yield based on the moles of ethyl nicotinate used. Since the dry crystalline solid product is not hygroscopic, but the wet solid may pick up water after filtration, filtration should be performed, for example, under nitrogen atmosphere.

EXAMPLE 2

EFFECT OF ANABASEINE, DMAB-ANABASEINE AND ANABASINE ON MEMORY-RELATED BEHAVIOR

A. Passive Avoidance Behavior

Male Sprague Dawley albino rats were used for all studies and were maintained in departmental animal facilities, using NIH guidelines for care of animals. Where lesioned animals were tested, lesions were induced in anesthetized animals by bilateral infusion of ibotenic acid (5 µg in 1 µl) or phosphate buffered saline (PBS) into the nucleus basalis region.

For passive avoidance behavior, animals received a moderately strong shock (0.8 m Amp) for 1 second after entering a dark room. After 24 hours, the animals were again tested to determine if they could remember to stay out of the dark room. Animals were only allowed 5 minutes to make their choice, when they were removed from the lighted chamber. For testing the effects of drugs in animals that were not lesioned, shocks were only 0.5 m Amp in intensity, and the animals were allowed 72 hours until they were tested after training. In all drug-treatment studies, the drugs were injected intraperitoneally in saline diluent 5 minutes before the trial and 5 minutes before the testing period.

Figure 2:
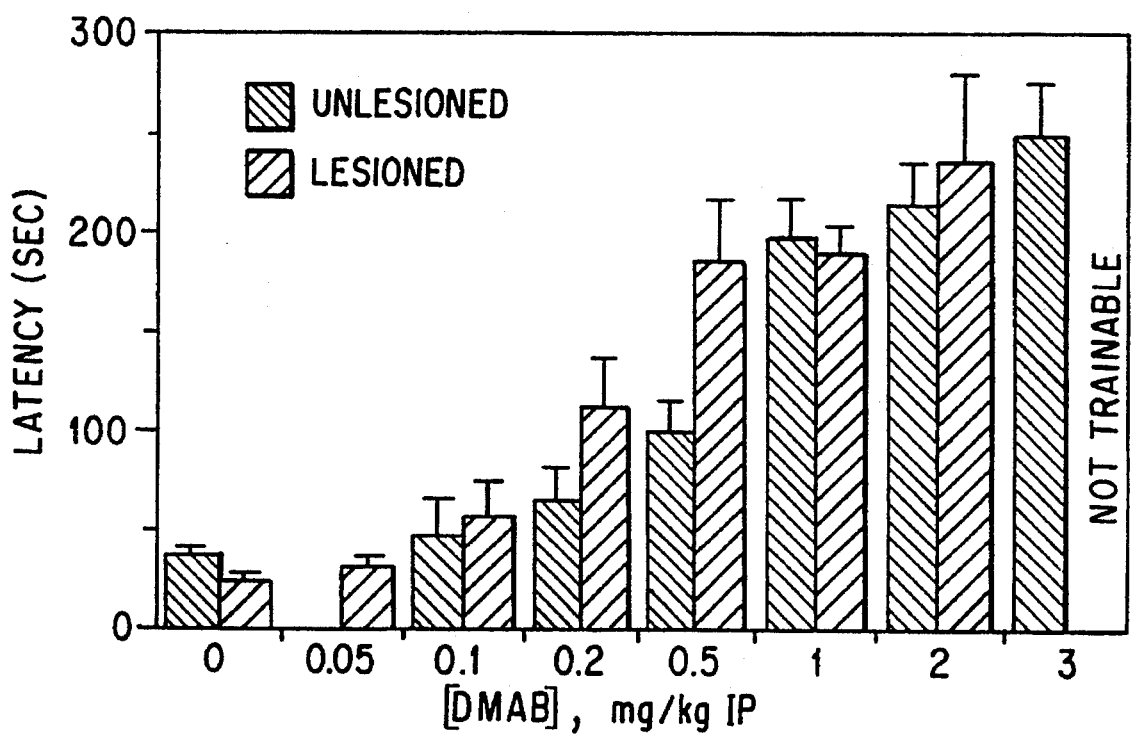
FIG. 2 Effects of NBM lesions on DMAB-anabaseine-induced improvement in passive avoidance behavior.

As shown in FIGS. 1 and 2, anabaseine and DMAB-anabaseine, respectively, were more potent in lesioned then in unlesioned animals. For nicotine, 0.05 mg/kg was effective in unlesioned animals, while 0.02 mg/kg was effective in lesioned animals. For anabaseine, a similar 2.5 fold shift was observed. For both of these drugs, the animals were also more sensitive after lesioning in that 0.2 mg/kg doses interfered with training or behavior. For DMAB-anabaseine, potency was increased between 2–2.5 fold by lesioning.

Figure 3:
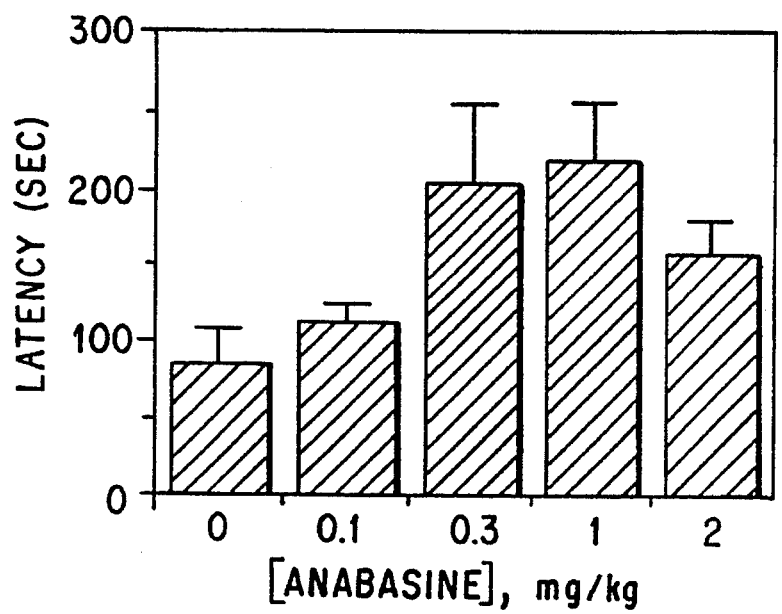
FIG. 3 Effects of anabasine on passive avoidance behavior.

The effect of (−)anabasine on passive avoidance was also determined using unlesioned animals (FIG. 3). In these experiments (−)anabasine was injected intraperitoneally 5 min. before training and testing in the passive avoidance apparatus. Only animals that trained within 300 sec the first time were used (i.e., those animals that entered the dark compartment and received a mild foot shock).

These results indicate that anabaseine, DMAB-anabaseine, and anabasine can improve this type of memory-related behavior, apparently by binding to and activating nicotine transmission, even in animals with reduced neocortical cholinergic activity. This latter state mimics that seen in Alzheimer's disease.

B. Radial Maze Testing

The 17 arm radial maze requires animals to remember a baited set of 8 arms out of the 17 total arms. At the start of each daily trial, rats are placed in the center of the maze and permitted to choose among the 17 arms until all 8 food rewards are taken or until fifteen minutes elapse. Those animals that reach a performance criteria of 17 arm choices on two consecutive days of testing during the first 14 days of testing are continued in testing for an additional 30 days. For such animals, only data collected after day 14 are used in the statistical analyses. Statistical analyses are done on 3 sets of data. The first is a measure of general learning: the percent correct choices (entries into baited arms) over the first 8 arm choices. The second is a measure of short term memory (working memory) calculated from the first 12 arm choices: the percent of choices into baited arms (containing food) over the total number of choices within the baited set. Working memory, an interatrial measure of short term memory, measured the rat's ability to remember which of the arms in the baited set were previously entered and the food reward taken. The third set of data measured long-term or reference memory and also was calculated from the first 12 arm choices. Reference memory, defined as an inter-trial measure, is the percent correct choices in the baited set over the total number of arm choices.

Two groups of aged rats were tested in the 17-arm radial maze. One group as given 0.2 mg/kg nicotine (n=5) and the other 2 mg/kg DMAB-anabaseine (n=5) at 15 minutes prior to each daily trial. The purpose of these injections was to determine if activation of nicotinic receptors (by nicotine or DMAB-anabaseine) can enhance the poor learning ability and long term memory of aged rats in this task.

Figure 4:
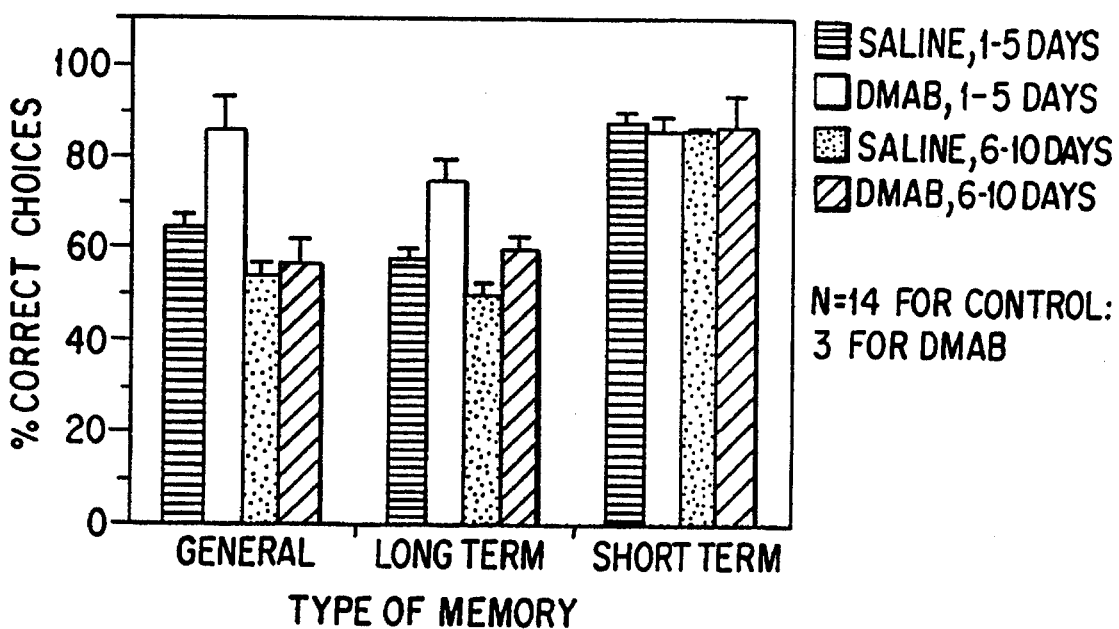
FIG. 4 Effect of DMAB-anabaseine on performance of aged rats in the 17-arm radial maze.

As shown in FIG. 4, DMAB improved a measure of long term memory without affecting the short term memory of the animals. This selective effect is sometimes typical of nicotine and other memory/learning paradigms.

C. Lashley III Maze Testing

The Lashley III maze tests an animal's ability to learn a series of left-right alternation turns. Six alternation errors are possible for any given daily trial; chance performance level is 3 errors per trial. Previous studies have shown that young adult sham operated animals quickly learn to reduce their number of alternation errors to near zero by the end of the test period. By contrast, 23 months old (Aged) sham operated animals made substantially more errors over the 25 days of testing. Moreover, bilateral nucleus basalis lesioning of aged rats resulted in an even greater learning deficit compared to aged, sham-lesioned animals. Therefore, both age- and lesion-induced learning deficits were observed. Nonetheless, all groups did improve their performance over time.

Figure 5:
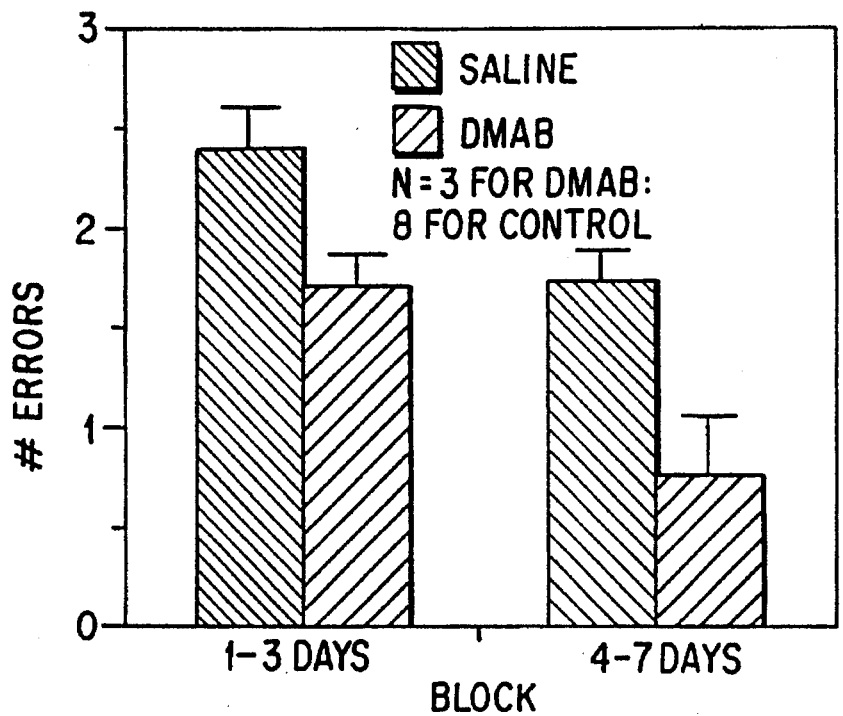
FIG. 5 Effect of DMAB-anabaseine on performance of aged rats in the Lashley III maze.

Aged animals injected with saline or DMAB-anabaseine were evaluated in the Lashley III maze (FIG. 5). When injected at a 2 mg/kg dose before training, DMAB reduced the number of errors that the aged animals made in this maze over the first two blocks of tests. This reflected an improvement in another memory-related behavior with this nicotine agonist.

EXAMPLE 3

EFFECT OF ANABASEINE AND DMAB-ANABASEINE ON NEUROTRANSMITTER RELEASE

Neurotransmitter release from synaptosomes provides a potential marker for receptor-activity at different types of nerve terminals. Neurotransmitter release from intact slices or minces provides a marker for receptor activity at many sites on the neuron. A comparison of the effects of nicotine and other drugs on synaptosomes versus slices provides some idea as to the location of nicotinic receptors on different types of cerebral cortical neurons, as well as their cellular location.

These different types of cerebral cortical transmitter systems have been tested. The first is the cholinergic; the procedures used to load cholinergic neurons or slices with newly synthesized [3H]ACh were described previously (Meyer, et al., 1987). The second is aspartate, an excitatory amino acid which, like glutamate, is associated with memory (long term potentiation) and neuropathology (e.g., stroke). The third type of neurotransmitter is GABA, which is the predominant transmitter in the cerebral cortex and is therefore very likely to receive cholinergic innervation.

In order to measure aspartate or GABA release, tissues were incubated with 100 nM [3H] aspartate or 250 nM [3h] GABA in Krebs Ringer buffer at 37° C. for 30 minutes, then washed them in ice cold buffer. All release-incubations were at 37° C. for 15 minutes in the presence or absence of 50 mM KCl (depolarization). Radiation accumulation was also measured in slices in order to express the released levels of transmitter as % of total transmitter, since slices were somewhat variable with respect to accumulation of label. K+ induced release of transmitter was determined by subtracting the basal release from that in the presence of the elevated K+, such that only the incremental release was determined.

Neurotransmitter levels (aspartate, glutamate) and enzyme levels were assayed as described by Arendash, et al., *Science*, 238:952, 1987. Nicotine, anabaseine, and DMAB-anabaseine were found to have no effect on the basal or 50 mM KCl induced release of newly synthesized [3H] ACh from synaptosomes. Also, no effect was seen on the release of [3H] aspartate from isolated terminals. Consequently, there do not appear to be nicotine receptors or aspartate terminals (or glutamate terminals, since aspartate may be taken and released from glutamate terminals) in the cerebral cortex.

Figure 6:
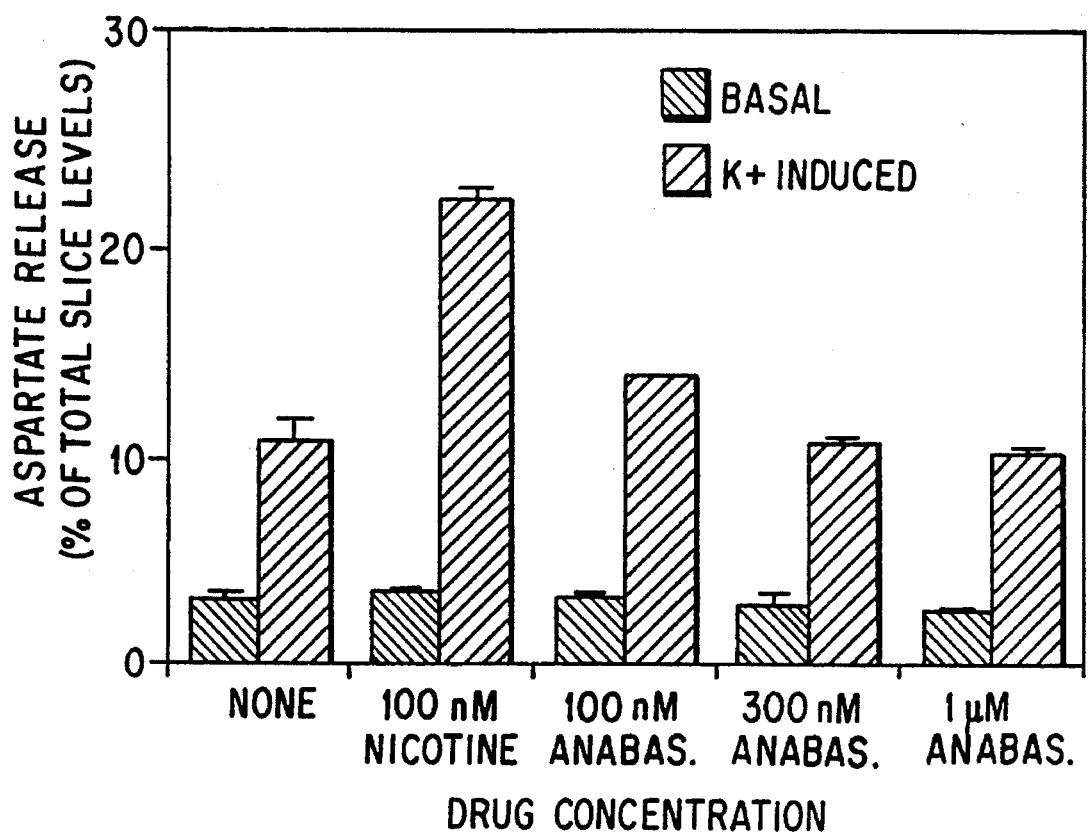
FIG. 6 Aspartate release from brain tissue exposed to anabaseine.

In studies on brain tissue slices, nicotine (100 nM) increased the K+ induced release of aspartate from slices without affecting the spontaneous release of transmitter (FIG. 6). The fact that nicotine can directly depolarize aspartate neurons without increasing basal release as well as K+ induced release is surprising. One hypothesis is that nicotine stimulates another type of neuron (presumably excitatory) to dis-inhibit the release of aspartate; this dis-inhibition would not be seen except when the aspartate neuron itself was activated by depolarization.

Figure 7:
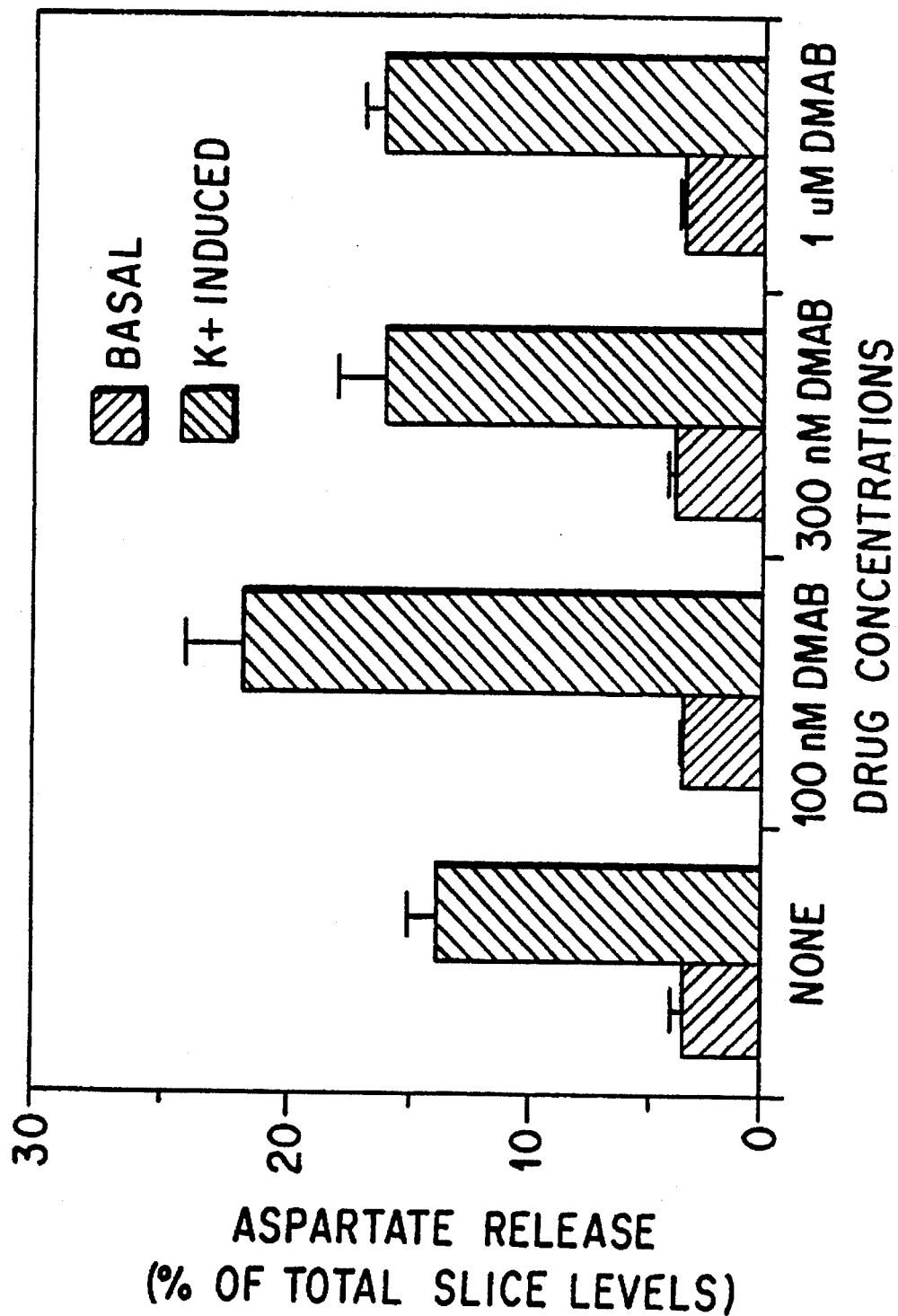
FIG. 7 Aspartate release from brain tissue exposed to DMAB-anabaseine.

Interestingly, anabaseine and DMAB-anabaseine (except at one low concentration) did not increase aspartate release in a dose-related manner (FIGS. 6 and 7). Thus, the effect on depolarization-induced aspartate release was correlated with inhibition of high affinity [3H] nicotine binding, not the inhibition of [3H]ACh or [3H]methcarbachol binding.

This pattern was also observed with [3H]ACh release and [3H]GABA release from cortical slices. Nicotine (100 nM) increased the K+ induced release of ACh but reduced the K+ induced GABA release from slices, while anabaseine (1 μM) had no effect on either process. Nicotine also increased basal ACh release, suggesting a direct excitatory effect on intrinsic cholinergic cell bodies (not terminals, from synaptosome studies described above). Thus, it appears that the ability of nicotinic types of compounds to modulate neurotransmitter release is not mediated through one of the receptors with high affinity for anabaseine, or DMAB-anabaseine.

EXAMPLE 4

Preparation of the Aminal of 2-Piperidone: 1-(Diethhylaminomethyl)-2-Piperidone (1)

2-Piperidone (10 g, 0.10 moles), 37% by wt. of aqueous formaldehyde (9.8 mL, 0.12 moles), and diethylamine (12.5 mL, 0.12 moles) were added together and heated to reflux while stirring. After 8 hours, the reaction product was concentrated under reduced pressure and 20 mL of brine was added. The aqueous phase was extracted 5 times with 50 mL portions of diethyl ether. The ether extracts were combined, dried with sodium sulfate and concentrated to yield 16.7 g of a slightly brown liquid. The product was purified by vacuum distillation with 14.7 g (80% yield) of the product distilling over at 113° C. at 3.1 mm of mercury pressure. $^1$H NMR (CDCl$_3$): δ4.05, (N—CH$_2$—N, s, 2H), 3.22 (CH$_2$, bm, 2H), 2.5 (CH$_2$—N, q, 4H), 2.25 (CH$_2$, bm, 2H), 1.7 (CH$_2$—CH$_2$, bm, 4H), 0.95 ppm (CH$_3$, t, 6H). HRMS (EI) Calcd for C$_{10}$H$_{20}$N$_2$O: 184.1576. Found: 15 184.1572.

Preparation of the Sodium salt of the Aminal of 3-Nicotinoyl-2-Piperidone (2):

To a solution of (1) (9.40 g, 0.0540 moles), ethyl nicotinate (7.4 mL, 0.054 moles), and toluene (50 mL), slowly was added a 60% dispersion in mineral oil of sodium hydride (4.3 g, 0.11 moles). A gas was evolved. The suspension was heated at reflux while stirring. After 4 hours another equivalent (2.1 g, 0.054 moles) of sodium hydride was added. After another 4 hours of stirring at reflux, the reaction was filtered. The collected solid (excess NaH) was destroyed by the cautious addition of ethanol. The filtrate was cooled to 0° C. and the product slowly precipitated out. The solution may need some agitation to get product to precipitate as it has a tendency to supersaturate. The product was collected by filtration and dried to give 16.2 g of a slightly yellow solid (97% yield). The solid is hydroscopic and slowly turned to a sticky orange material. The $^1$H NMR consisted of a mixture of enol and keto tautomers. $^1$H NMR (DMSO-d$_6$): δ9.2 (H2', keto, s), 8.75 (H2'+H6', enol, m), 8.6 (H6'keto, d), 8.3 (H4'keto, d), 7.85 (H4'enol, d), 7.4 (H5'keto, dd), 7.3 (H5'enol, dd), 4.4 (CH, keto, t), 4.25 (N—CH$_2$—N, enol, s), 4.15 (NCH$_2$—N, keto, d), 3.45 (m), 2.6 (CH$_2$CH$_3$, m), 2.5 (m), 2.2 (m), 2.05 (m), 1.8 (m) and 1.05 (m, CH$_3$).

Preparation of Anabaseine Dihydrochloride (3):

The sodium salt (2) (900 mg, 2.90 mmoles) was heated at reflux for 12 hours in a 5:1 mixture of concentrated HCl and acetone. The acetone was required in order to give product of better quality. The reaction was allowed to cool and NaCl was filtered off. The filtrate was diluted with 70 mL of isopropyl alcohol and allowed to sit at 0° C. The dihydrochloride crystallized out slowly to yield 500 mg of white needle-like crystals (mp 175°–179° C., decomp, 74% yield). $^1$H NMR (DMSO-d$_6$): δ9.15 ppm (H2', s, 1H), 8.95 (H6', d, 1H), 8.60 (H4', d, 1H), 8.1 (N—H, b, 2H), 7.85 (H5', dd, 1H), 3.2 (CH$_2$, m, 2H), 2.8 (CH$_2$, m, 2H), 1.62 ppm (CH$_2$, m, 4H). Anal. Calcd for C$_{10}$H$_{14}$N$_2$Cl$_2$•H$_2$O: C, 47.81; H, 6.42; N, 11.15. Found: C, 47.70; H, 6.42; N, 11.07.

The invention now being fully described, it will be apparent to one of ordinary skill in the art that many changes and modifications can be made without departing from the spirit or scope of the invention.

We claim:

1. A process for making an anabaseine salt, comprising the steps:

(a) reacting a piperidone aminal with an activated derivative of nicotinic acid under conditions suitable for formation of an aminal nicotinoyl piperidone salt having the formula:

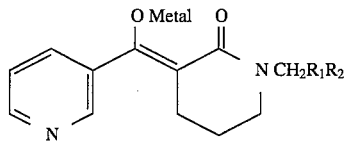

where R$_1$ and R$_2$ are lower alkyl, or where R$_1$ and R$_2$ form a morpholine or piperidine ring attached at the nitrogen and where the metal is a Group I alkaline metal; and (b) converting said aminal salt in the presence of strong acid to an anabaseine salt.

2. The process of claim 1 wherein the anabaseine salt is anabaseine dihydrochloride.

3. The process of claim 1 wherein the activated derivative of nicotinic acid is selected from the group consisting of nicotinic acid halides, nicotinic acid esters, and nicotinic acid anhydrides.

4. The process of claim 3 wherein the activated derivative of nicotinic acid is a nicotinic acid alkyl ester having from one to five carbon atoms in the alkyl group.

5. The process of claim 1 wherein the strong acid is mixed with a ketone cosolvent in molar excess relative to the sodium salt.

6. The process of claim 5 wherein the ratio of the cosolvent to the sodium salt is about to 5:1.

7. The process of claim 5 wherein the cosolvent is a low molecular weight ketone.

8. The process of claim 7 wherein the cosolvent is selected from the group consisting of acetone and methyl ethyl ketone.

9. The process of claim 1 wherein the aminal of piperidone is obtained by contacting piperidone with a secondary amine.

10. The process of claim 9 wherein the secondary amine is selected from the group consisting of diethylamine, morpholine and piperidine.

11. The process of claim 1 wherein the formaldehyde is an acetal or paraformaldehyde.

12. The process of claim 1 wherein the solvent is selected from the group consisting of toluene, 1,4-dioxane, tetrahydrofuran, ethylene glycol, dimethyl ether and toluene.

13. The process of claim 12 wherein the solvent is toluene.

14. The process of claim 1 wherein formation of said aminal nicotinyl piperidone salt is at an elevated temperature.

15. The process of claim 1 wherein the strong acid is hydrochloric acid.

16. A process for making an anabaseine salt, comprising the steps:

(a) reacting a 2-piperidone aminal with an activated derivative of 3-nicotinic acid under conditions suitable for formation of a salt of the aminal of 3-nicotinyl-2-piperidone; and (b) converting said aminal salt in the presence of a strong acid to form an anabaseine salt.

17. The method of claim 11 wherein the formaldehyde is anhydrous.

* * * * *